United States Patent [19]

Ries et al.

[11] Patent Number: 4,845,289

[45] Date of Patent: Jul. 4, 1989

[54] PROCEDURE FOR THE REMOVAL OR REDUCTION OF RESIDUAL TRIMETHYLAMINE ODOR FROM ITS REACTION PRODUCTS

[75] Inventors: Donald G. Ries, Richmond; Allan W. Smith, Sugarland, both of Tex.

[73] Assignee: Nalco Chemical Company, Naperville, Ill.

[21] Appl. No.: 161,554

[22] Filed: Feb. 29, 1988

[51] Int. Cl.$^4$ .............................................. C07C 85/26
[52] U.S. Cl. .................................... 564/296; 564/281; 564/285; 564/286; 564/292; 564/294
[58] Field of Search ............... 564/291, 292, 294, 295, 564/296, 281, 285, 286

[56] References Cited

U.S. PATENT DOCUMENTS

| | | | |
|---|---|---|---|
| 3,472,740 | 10/1969 | Boothe | 564/296 |
| 3,928,447 | 12/1975 | Chin et al. | 564/296 |
| 4,377,710 | 3/1981 | Seale et al. | 564/281 |

FOREIGN PATENT DOCUMENTS 62-447  1/1987  Japan .................................. 564/296

*Primary Examiner*—James H. Reamer
*Attorney, Agent, or Firm*—John G. Premo; Donald G. Epple; Anthony L. Cupoli

[57] ABSTRACT

A process for the removal or reduction of residual trimethyl amine odor resulting from the quaternization of a halogen containing precursor with trimethyl amine. Odor reduction is achieved by reacting the residual trimethyl amine with at least an equivalent amount of methyl chloride at a temperature of at least 50° C. for a period of time to convert substantially all of the trimethyl amine to tetramethyl ammonium chloride.

4 Claims, No Drawings

PROCEDURE FOR THE REMOVAL OR REDUCTION OF RESIDUAL TRIMETHYLAMINE ODOR FROM ITS REACTION PRODUCTS

INTRODUCTION

A variety of cationic chemical products containing one or more substituted trimethylammonium halide quaternary groups are produced by reacting trimethyl amine with a halogen containing precursor compound.

One such class of halogen containing precursor compounds, where the halogen is chloride, can be obtained from the reaction of one or more moles of epichlorohydrin with an active hydrogen compound. These chlorine containing precursor compounds can be illustrated by Formula I where R is the residue from an active hydrogen compound, and where n is an interger. Where n is more than 1, the product can be considered polymeric.

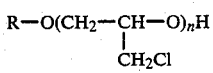
Formula I

Examples of quaternary products from such chlorine containing precursor compounds and trimethyl amine are the trimethyl amine quaternary from polyepichlorohydrin, the trimethyl amine quaternized products from the adduct of a mixture of $C_{12}$ to $C_{15}$ aliphatic alcohols and 1 to 2 moles of epichlorohydrin, and the trimethyl amine quaternized products described in U.S. Pat. No. 4,377,710, the disclosure of which is incorporated herein by reference.

Products of the type described in this patent are shown below as Formula II.

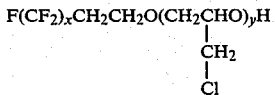
Formula II x is from 2–12 and y is from 1–20.

In these products as well as others, there frequently remains upon completion of the reaction excess trimethyl amine which is odoriferous and has undesirable toxological problems.

The residual trimethyl amine is difficult to remove completely from aqueous systems because of its high solubility in water, and extensive purging with an inert gas and/or removal of water is necessary to also remove substantial quantities of amine. This can be a time-consuming and energy intensive process.

The present invention provides a method for removing substantially all of the trimethyl amine from these products thereby rendering them odor-free and less toxic.

THE INVENTION

The invention comprises a process for the removal or reduction of residual trimethyl amine odor resulting from the quaternization of a halogen containing precursor with trimethyl amine which comprises reacting the residual trimethyl amine with at least an equivalent amount of methyl chloride at a temperature of at least 50° C. for a sufficient period of time to convert substantially all of the trimethyl amine to tetramethyl ammonium chloride. To insure a good removal of the trimethyl amine, at least a 5% excess of the methyl chloride is preferred.

The reaction of methyl chloride with residual trimethyl amine in products of the type described above is preferably conducted under pressure and at temperatures of at least 50° C. and usually at temperatures of 70° C. to 100° C. The reaction time may vary between 1 to 10 hours depending on reaction temperature and pressure. A typical reaction condition is about 5 hours at 75° C. In order for the methyl chloride to convert the trimethyl amine to tetramethylammonium chloride, the pH of the system must be adjusted, if necessary, to a pH of at least 8, more preferably 10-12, by adding a caustic material such as sodium hydroxide.

To illustrate the invention, the following is presented.

EXAMPLE I 300 g of an aqueous solution containing 70% by weight of a trimethyl amine quaternized polyepichlorohydrin and containing several percent residual trimethyl amine was placed in a 600 ml Parr Autoclave. Aqueous 50% sodium hydroxide was added dropwise to adjust the pH to about 11. The autoclave was sealed and approximately 15 g methyl chloride was charged to the autoclave. The autoclave was heated to 75° to 90° C. After 2 hours the autoclave was cooled; vented and the product removed. The pH was found to be about 2. Dilute (10%) aqueous sodium hydroxide was added dropwise to raise the pH to about 6. The product had no amine odor and no amine could be detected by $C_{13}$ NMR analysis.

Having thus described our invention, we claim:

1. A process for the removal of reduction of residual trimethyl amine odor in aqueous systems resulting from using trimethyl amine as a raw material in the production of chemical products resulting from the quaternization of a halogen-containing precursor with trimethyl amine which comprises reacting the residual trimethyl amine with at least an equivalent amount of methyl chloride at a temperature of at least 50° C. for a sufficient period of time to convert substantially all of the trimethyl amine to tetramethyl ammonium chloride.

2. The method of claim 1 wherein the chemical product is in the form of trimethyl amine quaternized polyepichlorohydrin.

3. The method of claim 1 wherein the chemical product is in the form of a trimethyl amine quaternized perflorocompound having the formula:

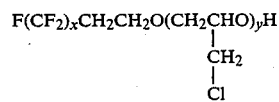

where x is from 2–12 and y is from 1–20.

4. The method of claim 1 wherein the chemical product is in the form of trimethyl amine quaternary from the adduct of an alcohol and epichlorohydrin having the formula:

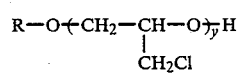

wherein R=$C_{12}$ to $C_{15}$ and y is 1 to 2.

* * * * *

UNITED STATES PATENT AND TRADEMARK OFFICE
CERTIFICATE OF CORRECTION

PATENT NO.  :  4,845,289
DATED       :  July 4, 1989
INVENTOR(S) :  DONALD G. RIES & ALLAN W. SMITH It is certified that error appears in the above-identified patent and that said Letters Patent is hereby corrected as shown below:

Column 2, Line 34, Claim 1

1. A process for the removal of reduction of residual

"LETTERS PATENT SHOULD READ AS:"

1. A process for the removal or reduction of residual

Signed and Sealed this

Fifteenth Day of May, 1990

Attest:

HARRY F. MANBECK, JR.

*Attesting Officer*     Commissioner of Patents and Trademarks